United States Patent
Sode et al.

(10) Patent No.: US 9,512,459 B2
(45) Date of Patent: Dec. 6, 2016

(54) GLUCOSE DEHYDROGENASE

(71) Applicant: ULTIZYME INTERNATIONAL LTD., Tokyo (JP)

(72) Inventors: Koji Sode, Tokyo (JP); Kazushige Mori, Tokyo (JP)

(73) Assignee: ULTIZYME INTERNATIONAL LTD., Tokyo (JP)

( * ) Notice: Subject to any disclaimer, the term of this patent is extended or adjusted under 35 U.S.C. 154(b) by 0 days.

(21) Appl. No.: 14/369,646

(22) PCT Filed: Dec. 28, 2012

(86) PCT No.: PCT/JP2012/008460
§ 371 (c)(1),
(2) Date: Jun. 27, 2014

(87) PCT Pub. No.: WO2013/099294
PCT Pub. Date: Jul. 4, 2013

(65) Prior Publication Data
US 2014/0356887 A1 Dec. 4, 2014

(30) Foreign Application Priority Data
Dec. 28, 2011 (JP) ................................. 2011-288830

(51) Int. Cl.
*C12Q 1/00* (2006.01)
*C12N 9/04* (2006.01)
*C12Q 1/54* (2006.01)
*C12Q 1/32* (2006.01)

(52) U.S. Cl.
CPC ............. *C12Q 1/006* (2013.01); *C12N 9/0006* (2013.01); *C12Q 1/001* (2013.01); *C12Q 1/32* (2013.01); *C12Q 1/54* (2013.01); *C12Y 101/00* (2013.01); *C12Y 101/9901* (2013.01)

(58) Field of Classification Search
CPC ... C12N 9/0006; C12Y 101/9901; C12Q 1/32; C12Q 1/006
USPC ........................... 435/14, 190, 320.1, 252.33
See application file for complete search history.

(56) References Cited

U.S. PATENT DOCUMENTS

| 2009/0181408 A1 | 7/2009 | Tanaka et al. |
| 2010/0297743 A1 | 11/2010 | Omura et al. |
| 2012/0122130 A1 | 5/2012 | Omura et al. |
| 2013/0168263 A1 | 7/2013 | Sode et al. |

FOREIGN PATENT DOCUMENTS

| EP | 2 241 621 A1 | 10/2010 |
| JP | 2007-289148 A | 11/2007 |
| JP | 2008-35747 A | 2/2008 |
| JP | 2008-35748 A | 2/2008 |
| JP | 2008-178380 A | 8/2008 |
| JP | 2010-51312 A | 3/2010 |
| JP | 2010-54503 A | 3/2010 |
| JP | 2010-57427 A | 3/2010 |
| WO | WO 2004/058958 A1 | 7/2004 |
| WO | WO 2006/101239 A1 | 9/2006 |
| WO | WO 2007/011610 A2 | 1/2007 |
| WO | WO 2007/139013 A1 | 12/2007 |
| WO | WO 2012/001976 A1 | 1/2012 |

OTHER PUBLICATIONS

Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Extended European Search Report issued Dec. 23, 2015, in European Patent Application No. 12863747.7.
International Search Report for PCT/JP2012/008460 mailed on Mar. 19, 2013.
Mori et al., "Screening of Aspergillus-derived FAD-glucose dehydrogenases from fungal genome database", Biotechnol Lett. vol. 33, 2011, pp. 2255-2263.
Rolke et al., "Functional analysis of H2O2-generating systems in Botrytis cinerea: the major Cu—Zn-superoxide dismutase (BCSOD1) contributes to virulence on French bean, wheras a glucose oxidase (BCGOD1) is dispensable", Molecular Plant Pathology, vol. 5, No. 1, 2004, pp. 17-27.
Communication Pursuant to Rule 164(1) EPC issued Oct. 9, 2015, in European Patent Application No. 12863747.7.

* cited by examiner

*Primary Examiner* — Robert Mondesi
*Assistant Examiner* — MD. Younus Meah
(74) *Attorney, Agent, or Firm* — Birch, Stewart, Kolasch & Birch, LLP

(57) ABSTRACT

Amino acid mutation(s) can be introduced to *Sclerotinia sclerotiorum*- or *Aspergillus niger*-derived glucose dehydrogenase to obtain a glucose dehydrogenase variant with significantly enhanced productivity in *E. coli*. The glucose dehydrogenase of the present invention is low reactive with xylose.

16 Claims, No Drawings

GLUCOSE DEHYDROGENASE

RELATED APPLICATION

The present application claims the priority based on Japanese Patent Application No. 2011-288830 (filed on Dec. 28, 2011), the contents of which are incorporated herein by reference.

TECHNICAL FIELD

The present invention relates to glucose dehydrogenase (FAD-GDH) whose coenzyme is flavin adenine dinucleotide, a method for producing the same, and use of the same in the quantification of glucose.

BACKGROUND ART

Blood glucose concentrations serve as an important marker for diabetes mellitus. Heretofore, enzymatic methods using glucose oxidase (GOD), glucose-6-phosphate dehydrogenase (G6PDH), glucose dehydrogenase (PQQGDH) whose coenzyme is pyrroloquinoline quinone, or the like have been used for measuring glucose concentrations. GOD, however, requires oxygen as an electron acceptor. Its measurement value is therefore disadvantageously influenced by the level of dissolved oxygen in a test sample. G6PDH inevitably involves adding its coenzyme NAD(P) to the reaction system and disadvantageously complicates the detection system. Furthermore, PQQGDH has unfavorable high activity against maltose due to its low glucose selectivity, though this enzyme advantageously has high oxidizing activity against glucose, which eliminates the need of oxygen as an electron acceptor. Thus, there has been a demand for a novel enzyme that can be used as a sensing element for glucose sensors. In addition, the enzyme is desired to have such low reactivity with xylose that blood sugar levels can be accurately measured even during a xylose absorption test.

Fungi have been classically known to have glucose dehydrogenase (e.g., Biochim biophys Acta. 139 (2), p. 265-276, 1967). Aspergillus- or Penicillium-derived glucose dehydrogenase and glucose concentration measurement using this enzyme are disclosed in, for example, the following patent literatures (Japanese Patent Laid-Open No. 2007-289148, Japanese Patent Laid-Open No. 2008-178380, Japanese Patent Laid-Open No. 2008-035748, Japanese Patent Laid-Open No. 2008-035747, WO2007/11610, WO2004/058958, WO2006/101239, and WO2007/139013). Most of fungus-derived enzymes, however, are glycoproteins and thus require glycosylation for expressing their functions. Particularly, extracellularly secreted enzymes, such as glucose oxidase, are highly glycosylated. These fungus-derived glycoproteins are therefore very difficult to produce recombinantly using E. coli. Since fungus-derived glucose dehydrogenase is also an extracellularly secreted protein, this fungus-derived glucose dehydrogenase is difficult to express recombinantly in E. coli. Even if this enzyme can be expressed in such a manner, the enzyme has unfavorable low yields per unit volume of cultures due to its low productivity (e.g., Biotechnol. Lett. Volume 33, Number 11, p. 2255-2263, 2011).

All references cited herein are described below. The contents described in these literatures are incorporated herein by reference in their entirety.

CITATION LIST

Patent Literature

Patent Literature 1: Japanese Patent Laid-Open No. 2007-289148
Patent Literature 2: Japanese Patent Laid-Open No. 2008-178380
Patent Literature 3: Japanese Patent Laid-Open No. 2008
Patent Literature 4: Japanese Patent Laid-Open No. 2008-035747
Patent Literature 5: WO2007/11610
Patent Literature 6: WO2004/058958
Patent Literature 7: WO2006/101239
Patent Literature 8: WO2007/139013

Non Patent Literature

Non Patent Literature 1: Rolke et al., Mol Plant Pathol. 5 (1), p. 17-27, 2004
Non Patent Literature 2: Biotechnol. Lett. Volume 33, Number 11, p. 2255-2263, 2011

SUMMARY OF INVENTION

Technical Problem

An object of the present invention is to provide a novel enzyme having much higher productivity than that of conventional glucose dehydrogenase.

Solution to Problem

The present inventors have isolated the genes of Sclerotinia sclerotiorum-derived glucose dehydrogenase and Aspergillus niger-derived glucose dehydrogenase and further substituted their particular amino acid residues. As a result, the present inventors have found that this substitution significantly enhances the productivity of recombinant expression in E. coli.

Specifically, the present invention provides a protein comprising the amino acid sequence represented by SEQ ID NO: 1, or a protein comprising an amino acid sequence derived from the amino acid sequence represented by SEQ ID NO: 1 by the deletion, substitution, or insertion of one or more amino acid residues and having glucose dehydrogenase activity, wherein the protein has an amino acid mutation S529G, N191X (wherein X represents K, S, R, or E), or G69X (wherein X represents A, H, N, C, D, F, K, L, M, N, or R), or a combination thereof. Preferably, the protein of the present invention further has one or more mutations selected from the group consisting of Y70F or Y70M, G71S, A73X (wherein X represents E, P, M, T, or C), M112C or M112L, A113F or A113S, Y521F, S523P, F525W or F525Y, P527X (wherein X represents M, I, Q, V, or Y), A182R, S505P, V571C, N46E, N240E, N274E, N275K, and N370K or N370E. Particularly preferably, the protein of the present invention is a protein comprising the amino acid sequence represented by SEQ ID NO: 1, wherein the protein has an amino acid mutation selected from the group consisting of N191K/S529G, N191S/S529G, N191R/S529G, and N191E/S529G. Further preferably, the protein of the present invention is a protein comprising the amino acid sequence represented by SEQ ID NO: 1, wherein the protein has an amino acid mutation selected from the group consisting of N191K/S529G/G69X (wherein X represents A, H, N, C, D, F, K, L, M, N, or R), N191K/S529G/Y70F, N191K/S529G/F525Y, N191K/S529G/P527Y, N191K/S529G/P527V, N191K/ S529G/P527Y, N191K/S529G/F525Y/P527Y, N191K/ S529G/F525Y/P527Y/G69A, and N191K/S529G/S505P. Also preferably, the protein of the present invention is a protein comprising the amino acid sequence represented by SEQ ID NO: 1, wherein the protein has an amino acid mutation selected from the group consisting of N191K/ S529G/S505P/N46E, N191K/S529G/S505P/N240E, N191K/S529G/S505P/N274E, N191K/S529G/S505P/ N275E, N191K/S529G/S505P/N370K, and N191K/S529G/ S505P/N370E.

The present invention further provides any of the above proteins, wherein in the protein comprising the amino acid sequence represented by SEQ ID NO: 1, 16 residues are deleted from the N-terminal sequence thereof, and the Ser residue at position 17 is substituted by Met. The present invention also provides any of the above proteins, wherein in the protein comprising the amino acid sequence represented by SEQ ID NO: 1, 23 residues are deleted from the N-terminal sequence thereof, and Met-Thr-Asp-Ser-Thr-Leu-Asn, Met-Thr-Asp-Ser-Thr-Leu-Asn, Met-Asn-Thr-Thr-Thr-, or Met-Ala-Pro-Glu- is added.

In another aspect, the present invention provides a protein comprising the amino acid sequence represented by SEQ ID NO: 2, or a protein comprising an amino acid sequence derived from the amino acid sequence represented by SEQ ID NO: 2 by the deletion, substitution, or insertion of one or more amino acid residues and having glucose dehydrogenase activity, wherein the protein has an amino acid mutation E195K, Q196X (wherein X represents E, D, or R), Y524F, P526X (wherein X represents G, V, I, F, Y, S, T, C, M, H, or Q), N368K, or T522S, or a combination thereof. Preferably, the present invention provides a protein comprising the amino acid sequence represented by SEQ ID NO: 2, wherein the protein has an amino acid mutation selected from the group consisting of E195K/Q196X (wherein X represents E, D, or R), E195K/Q196E/G73A, E195K/ Q196E/S75G, E195K/Q196E/G73A/S75G, E195K/Q196E/ S69E/N70D/G73A, E195K/Q196E/Y524F, E195K/Q196E/ P526X (wherein X represents G, V, I, F, Y, S, T, C, M, H, or Q), E195K/Q196E/G73A/Y524F, E195K/Q196E/G73A/ P526X (wherein X represents I, F, S, or M), E195K/Q196E/ G73A/S75G/Y524F, E195K/Q196E/G73A/S75G/P526X (wherein X represents I, F, Y, S, or M), N368K/T522S, and N368K/T522S/E195K/Q196E. Particularly preferably, the protein of the present invention has an amino acid mutation selected from the group consisting of E195K/Q196E/G73A/ S75G/P526M, E195K/Q196E/Y524F, E195K/Q196E/ P526X, E195K/Q196E/S69E/N70D/G73A, E195K/Q196E/ G73A/S75G, E195K/Q196E/S75G, and E195K/Q196E/ G73A.

The present invention further provides any of the above proteins, wherein in the protein comprising the amino acid sequence represented by SEQ ID NO: 2, 20 residues are deleted from the N-terminal sequence thereof, and the Ala residue at position 21 is substituted by Met. The present invention also provides any of the above proteins, wherein in the protein comprising the amino acid sequence represented by SEQ ID NO: 2, 26 residues are deleted from the N-terminal sequence thereof, and Met-Thr-Asp-Ser-Thr-Leu-Asn or Met-Asn-Thr-Thr-Thr- is added.

In an alternative aspect, the present invention provides a gene encoding the glucose dehydrogenase of the present invention, a recombinant vector containing the gene, and a transformant or transductant obtained by transformation with the recombinant vector. The present invention also provides a method for producing glucose dehydrogenase, comprising culturing the transformant obtained by transformation with the recombinant vector containing the gene encoding the glucose dehydrogenase of the present invention, and collecting glucose dehydrogenase from the culture.

In a further alternative aspect, the present invention provides a method for analyzing glucose, comprising measuring a glucose concentration in a sample using the glucose dehydrogenase of the present invention. The present invention also provides a glucose assay kit comprising the glucose dehydrogenase of the present invention. The present invention also provides an enzyme electrode comprising the glucose dehydrogenase of the present invention immobilized on an electrode surface, and a glucose sensor comprising the enzyme electrode as a working electrode.

In a further alternative aspect, the present invention provides a biosensor for glucose measurement insusceptible to dissolved oxygen, wherein the biosensor employs a protein comprising the amino acid sequence represented by SEQ ID NO: 1, or a glucose dehydrogenase which comprises an amino acid sequence derived from the amino acid sequence represented by SEQ ID NO: 2 by the deletion, substitution, or insertion of one or more amino acid residues, has glucose dehydrogenase activity without exhibiting glucose oxidase activity, and has 20% or less reactivity with xylose with respect to reactivity thereof with glucose.

DESCRIPTION OF EMBODIMENTS

*Sclerotinia sclerotiorum*-Derived FAD-GDH

The present invention is directed to *Sclerotinia sclerotiorum*-derived glucose dehydrogenase (GenBank XP_001584680) as an enzyme to be recombinantly expressed. The amino acid sequence of this enzyme is shown in SEQ ID NO: 1. The genomic sequence of *Sclerotinia sclerotiorum* is publicly available.

*Aspergillus niger*-Derived FAD-GDH

The present invention is also directed to *Aspergillus niger*-derived glucose dehydrogenase (GenBank XP_001394544) as an enzyme to be recombinantly expressed. The amino acid sequence of this enzyme is shown in SEQ ID NO: 2. The genomic sequence of *Aspergillus niger* is publicly available. Also, the recombinant production of this enzyme is described in Biotechnol. Lett. Volume 33, Number 11, p. 2255-2263, 2011, which has reported that the protein is glucose dehydrogenase (GDH).

The glucose dehydrogenase (GDH) is useful as a sensing element for biosensors for glucose measurement, because this enzyme, unlike glucose oxidase (GOD), is insusceptible to dissolved oxygen in glucose measurement. The amino acid sequence represented by SEQ ID NO: 1 has approximately 30 to 60% sequence identity to the amino acid sequence of known fungus-derived glucose dehydrogenase and has approximately 57% sequence identity to, for example, the amino acid sequence of *Aspergillus oryzae* TI strain-derived glucose dehydrogenase (GenBank ACW04779.1).

In the present invention, Ssc refers to *Sclerotinia sclerotiorum*-derived glucose dehydrogenase (GenBank XP_001584680). In the present invention, a gene encoding the amino acid sequence of Ssc-n1, Ssc-n2, Ssc-n3, or Ssc-n4 was prepared for the efficient recombinant expression of Ssc in *E. coli*. In the present specification, the following 4 types of designations of Ssc are used on the basis of difference in their N-terminal sequences:

Ssc-n1

This designation refers to an Ssc protein in which 16 residues are deleted from the N-terminal sequence of the primary structure of Ssc described in the genomic database (*Sclerotinia sclerotiorum*; GenBank XP_001584680; shown in SEQ ID NO: 1), and the Ser residue at position 17 is substituted by Met.

Ssc-n2

This designation refers to an Ssc protein in which 23 residues are deleted from the N-terminal sequence of the primary structure of Ssc described in the genomic database (*Sclerotinia sclerotiorum*; GenBank XP_001584680; shown in SEQ ID NO: 1), and Met-Thr-Asp-Ser-Thr-Leu-Asn is added.

Ssc-n3

This designation refers to an Ssc protein in which 23 residues are deleted from the N-terminal sequence of the primary structure of Ssc described in the genomic database (*Sclerotinia sclerotiorum*; GenBank XP_001584680; shown in SEQ ID NO: 1), and Met-Asn-Thr-Thr-Thr- is added.

Ssc-n4

This designation refers to an Ssc protein in which 23 residues are deleted from the N-terminal sequence of the primary structure of Ssc described in the genomic database (*Sclerotinia sclerotiorum*; GenBank XP_001584680; shown in SEQ ID NO: 1), and Met-Ala-Pro-Glu- is added.

In the present invention, Ang refers to *Aspergillus niger*-derived glucose dehydrogenase (GenBank XP_001394544). In the present invention, a gene encoding the amino acid sequence of Ang-n1, Ang-n2, or Ang-n3 was prepared for the efficient recombinant expression of Ang in *E. coli*. In the present specification, the following 3 types of designations of Ang are used on the basis of difference in their N-terminal sequences:

Ang-n1

This designation refers to an Ang protein in which 20 residues are deleted from the N-terminal sequence of the primary structure of Ang described in the genomic database (*Aspergillus niger*; GenBank XP_001394544; shown in SEQ ID NO: 2), and the Ala residue at position 21 is substituted by Met.

Ang-n2

This designation refers to an Ang protein in which 26 residues are deleted from the N-terminal sequence of the primary structure of Ang described in the genomic database (*Aspergillus niger*; GenBank XP_001394544; shown in SEQ ID NO: 2), and Met-Thr-Asp-Ser-Thr-Leu-Asn is added.

Ang-n3

This designation refers to an Ang protein in which 26 residues are deleted from the N-terminal sequence of the primary structure of Ang described in the genomic database (*Aspergillus niger*; GenBank XP_001394544; shown in SEQ ID NO: 2), and Met-Asn-Thr-Thr-Thr- is added.

When used herein, the enzyme with high productivity in *E. coli* means an enzyme molecule having high enzymatic activity (U/L) per unit volume of a culture solution when the enzyme is isolated from cultures after recombinant expression with *E. coli* as a host. The high productivity allows the enzyme to be recombinantly produced at lower cost using a smaller culturing apparatus. The productivity of an enzyme is based on the amino acid sequence of the enzyme and comprehensively reflects difference in water solubility as a protein, difference in folding efficiency, difference in enzymatic activity per unit amount of protein, difference in stability of the enzyme, etc. In addition, the amino acid sequence of the enzyme is also involved in the rate of recombinant expression in a host per unit volume of a culture solution, the ease of formation of inclusion bodies, the stability of the enzyme in the fungus body and during purification steps, etc.

*Sclerotinia sclerotiorum*-Derived FAD-GDH Variant

The present inventors have found that: an FAD-GDH variant having a mutation N191K or S529G or a double mutation N191K/S529G in the amino acid sequence represented by SEQ ID NO: 1 exhibits higher productivity in *E. coli* than that of wild-type FAD-GDH; and, particularly, an FAD-GDH variant having the double mutation N191K/S529G exhibits high productivity as well as high enzymatic activity. In the present specification, the position of each amino acid mutation in the amino acid sequence of *Sclerotinia sclerotiorum*-derived FAD-GDH is numbered with Met at position 1 in the amino acid sequence of SEQ ID NO: 1 as 1. In the present specification, the mutation or substitution of an amino acid is indicated by the original amino acid residue, the position of the amino acid, and an amino acid residue after substitution in this order. For example, "S529G" represents that Ser at position 529 is replaced with Gly. Combination in a double or more mutation is indicated by the symbol "/".

The *Sclerotinia sclerotiorum*-derived FADG-GDH variant is preferably a protein having an amino acid mutation S529G, N191X (wherein X represents K, S, R, or E), or G69X (wherein X represents A, H, N, C, D, F, K, L, M, N, or R), or a combination thereof. Preferably, the protein further has one or more mutations selected from the group consisting of Y70F or Y70M, G71S, A73X (wherein X represents E, P, M, T, or C), M112C or M112L, A113F or A113S, Y521F, S523P, F525W or F525Y, P527X (wherein X represents M, I, Q, V, or Y), A182R, S505P, V571C, N46E, N240E, N274E, N275K, and N370K or N370E. Preferably, the protein has an amino acid mutation selected from the group consisting of N191K/S529G, N191S/S529G, N191R/S529G, and N191E/S529G, among these multiple mutations. In terms of a more preferred multiple mutation, the protein has an amino acid mutation selected from the group consisting of N191K/S529G/G69X (wherein X represents A, H, N, C, D, F, K, L, M, N, or R), N191K/S529G/Y70F, N191K/S529G/F525Y, N191K/S529G/P527Y, N191K/S529G/P527V, N191K/S529G/P527Y, N191K/S529G/F525Y/P527Y, N191K/S529G/F525Y/P527Y/G69A, and N191K/S529G/S505P. In terms of a further preferred multiple mutation, the protein has an amino acid mutation selected from the group consisting of, for example, N191K/S529G/S505P/N46E, N191K/S529G/S505P/N240E, N191K/S529G/S505P/N274E, N191K/S529G/S505P/N275E, N191K/S529G/S505P/N370K, and N191K/S529G/S505P/N370E.

Each of these FAD-GDH variants is preferably a protein comprising the amino acid sequence represented by SEQ ID NO: 1, wherein 16 residues are deleted from the N-terminal sequence thereof, and the Ser residue at position 17 is substituted by Met, or a protein comprising the amino acid sequence represented by SEQ ID NO: 1, wherein 23 residues are deleted from the N-terminal sequence thereof, and Met-Thr-Asp-Ser-Thr-Leu-Asn, Met-Thr-Asp-Ser-Thr-Leu-Asn, Met-Asn-Thr-Thr-Thr-, or Met-Ala-Pro-Glu- is added, the protein having any of these mutations and multiple mutations.

Moreover, these *Sclerotinia sclerotiorum*-derived FAD-GDH variants had higher selectivity for glucose relative to xylose than that of *Aspergillus oryzae* TI strain-derived FAD-GDH.

*Aspergillus niger*-Derived FAD-GDH Variant

The present inventors have found that: an FAD-GDH variant having a mutation E195K, Q196E, N368K, or T522S or a double mutation E195K/Q196E or N368K/T522S in the amino acid sequence represented by SEQ ID NO: 2 exhibits higher productivity in *E. coli* than that of wild-type FAD-GDH; and, particularly, an FAD-GDH variant having the double mutation E195K/Q196E exhibits high productivity as well as high enzymatic activity. In the present specification, the position of each amino acid mutation in the amino acid sequence of *Aspergillus niger*-derived FAD-GDH is numbered with Met at position 2 in the amino acid sequence of SEQ ID NO: 1 as 1. In the present specification, the mutation or substitution of an amino acid is indicated by the original amino acid residue, the position of the amino acid, and an amino acid residue after substitution in this order. For example, "E195K represents that Glu at position 195 is replaced with Lys. Combination in a double or more mutation is indicated by the symbol "/".

The *Aspergillus niger*-derived FADG-GDH variant is preferably a protein having an amino acid mutation E195K, Q196X (wherein X represents E, D, or R), Y524F, P526X (wherein X represents G, V, I, F, Y, S, T, C, M, H, or Q), N368K, or T522S, or a combination thereof. Preferred examples of a multiple mutation include E195K/Q196X (wherein X represents E, D, or R), E195K/Q196E/G73A, E195K/Q196E/S75G, E195K/Q196E/G73A/S75G, E195K/Q196E/S69E/N70D/G73A, E195K/Q196E/Y524F, E195K/Q196E/P526X (wherein X represents G, V, I, F, Y, S, T, C, M, H, or Q), E195K/Q196E/G73A/Y524F, E195K/Q196E/G73A/P526X (wherein X represents I, F, S, or M), E195K/Q196E/G73A/S75G/Y524F, E195K/Q196E/G73A/S75G/P526X (wherein X represents I, F, Y, S, or M), N368K/T522S, and N368K/T522S/E195K/Q196E. The multiple mutation is particularly preferably E195K/Q196E/G73A/S75G/P526M, E195K/Q196E/Y524F, E195K/Q196E/P526X, E195K/Q196E/S69E/N70D/G73A, E195K/Q196E/G73A/S75G, E195K/Q196E/S75G, or E195K/Q196E/G73A.

Each of these FAD-GDH variants is more preferably a protein comprising the amino acid sequence represented by SEQ ID NO: 2, wherein 20 residues are deleted from the N-terminal sequence thereof, and the Ala residue at position 21 is substituted by Met, or a protein comprising the amino acid sequence represented by SEQ ID NO: 2, wherein 26 residues are deleted from the N-terminal sequence thereof, and Met-Thr-Asp-Ser-Thr-Leu-Asn or Met-Asn-Thr-Thr-Thr- is added, the protein having any of these mutations and multiple mutations.

These *Aspergillus niger*-derived FAD-GDH variants had higher selectivity for glucose relative to xylose than that of *Aspergillus oryzae* TI strain-derived FAD-GDH.

Method for Producing FAD-GDH

The FAD-GDH of the present invention can be produced by recombinant expression using an approach well known in the art. The sequences of genes encoding *Sclerotinia sclerotiorum* and *Aspergillus niger*-derived natural FAD-GDHs can be readily determined on the basis of the amino acid sequences described in SEQ ID NOs: 1 and 2, respectively. The gene encoding each FAD-GDH may be cloned from the genome of *Sclerotinia sclerotiorum* or *Aspergillus niger* or may be produced by PCR using a series of chemically synthesized oligonucleotides. Alternatively, the gene may be totally synthesized using an automatic DNA synthesizer or the like. Desirably, the gene sequence is appropriately designed or altered after selection of codons to achieve a higher expression level in the host organism used. The feature of codon usage in a particular host organism is well known in the art.

The gene encoding the FAD-GDH variant of the present invention can be constructed from the natural FAD-GDH-encoding gene by the substitution of a nucleotide sequence encoding amino acid residue(s) to be substituted by a nucleotide sequence encoding desired amino acid residue(s). Such site-directed substitution of a nucleotide sequence is carried out by various methods well known in the art and can be performed, for example, by PCR using appropriately designed primers. Alternatively, a gene encoding the amino acid sequence of the variant may be totally synthesized.

In the FAD-GDH of the present invention, one or more of amino acid residues other than those described above may be deleted or substituted, or different amino acid residue(s) may be added, as long as the resulting protein has the desired glucose dehydrogenase activity. Preferably, such an FAD-GDH variant has at least 80% sequence identity to the amino acid sequence of natural FAD-GDH. The sequence identity is preferably at least 85%, more preferably at least 90%, further preferably at least 95%.

The gene thus obtained is inserted to appropriate vectors for expression, with which an appropriate host (e.g., *E. coli*) is transformed. Many vector-host systems for expressing foreign proteins are known in the art. Various hosts, for example, bacteria, yeasts, or cultured cells can be used. If the production of glycosylated glucose dehydrogenase is desired, eukaryotic cells are used as the host. The obtained transformants are cultured according to a standard method, and FAD-GDH can be recovered from the cells or the culture solution.

In a preferred aspect of the present invention, *E. coli* transformants are cultured in a medium described as ZYP broth in F. William Studier et al., Protein Expression and Purification (2005) (hereinafter, referred to as a medium A). Specifically, this medium is based on an LB medium generally used as a medium for *E. coli* and further supplemented with 0.5% glycerol, 0.05% glucose, 0.2% alpha-lactose, 25 mM (NH4)2SO4, 100 mM KH2PO4, 100 mM NaHPO4, and 1 mM MgSO4.

A recombinant protein is expressed by culture at 15° C. to 25° C., preferably approximately 20° C., in the medium A. This can yield higher productivity compared with use of an IPTG induction method routinely used. In addition, the mutated enzyme of the present invention can be coexpressed with chaperones GroEL and GroES, which are known to promote protein folding, to obtain further higher productivity. The coexpression with the chaperones can be performed, for example, by: transferring expression vectors containing the gene encoding the mutated enzyme of the present invention, together with vectors that permit expression of GroEL and GroES genes under the induction with arabinose (e.g., a commercially available chaperone vector pGro7, Takara Bio Inc.), to *E. coli*, followed by culture; and adding arabinose to the transformants grown to some extent to induce the expression of the chaperones.

The recombinant FAD-GDH thus obtained can be purified using an arbitrary purification approach known in the art, for example, gel filtration, ion-exchanged chromatography, affinity chromatography, liquid chromatography, filtration, ultrafiltration, salting out, solvent precipitation, immunoprecipitation, gel electrophoresis, isoelectric focusing, or dialysis.

Method for Measuring Enzymatic Activity

The FAD-GDH of the present invention has the effect of catalyzing reaction through which glucose is oxidized with FAD as a coenzyme to form gluconolactone. The glucose dehydrogenase activity of the FAD-GDH of the present invention can be measured through the color reaction of a redox dye by the quantification of the amount of FAD reduced along with the dehydrogenase-mediated oxidation of glucose. For example, PMS (phenazine methosulfate), DCIP (2,6-dichlorophenolindophenol), potassium ferricyanide, or ferrocene can be used as a chromogenic reagent. Also, the glucose-oxidizing activity of the FAD-GDH of the present invention can be measured by the quantification of hydrogen peroxide formed through the reaction of the dehydrogenase with a substrate. The hydrogen peroxide can be assayed by the measurement of time-dependent change in the absorbance of a dye formed using, for example, peroxidase, a Trinder reagent (TODB), and 4-aminoantipyrine.

Glucose Selectivity

The glucose selectivity of the FAD-GDH of the present invention can be evaluated by: measuring its enzymatic activity using various sugars such as mannose, galactose, xylose, lactose, and maltose as substrates; and examining relative activity to activity against glucose as a substrate.

The FAD-GDH of the present invention was highly selective for glucose and had reactivity, particularly with maltose and galactose, at levels equal to or lower than the measurement limits. Thus, an assay kit or an enzyme sensor prepared using the FAD-GDH of the present invention is highly selective in terms of glucose measurement and is advantageously capable of detecting glucose with high sensitivity in a test sample that contains or may contain other sugars such as maltose.

A further feature of the FAD-GDH of the present invention is its low reactivity with xylose. This provides the advantage that blood sugar levels can be accurately measured even during a xylose absorption test.

Glucose Assay Kit

The present invention also provides a glucose assay kit comprising the FAD-GDH according to the present invention. The glucose assay kit of the present invention comprises the FAD-GDH according to the present invention in an amount sufficient for at least one run of the assay. Typically, the kit comprises a buffer solution necessary for the assay, a mediator, a glucose standard solution for calibration curve preparation, and instruction of usage, in addition to the FAD-GDH of the present invention. The FAD-GDH according to the present invention can be provided in various forms, for example, as a freeze-dried reagent or as a solution in an appropriate preservation solution.

Glucose Sensor

The present invention also provides an enzyme electrode comprising the FAD-GDH according to the present invention immobilized on the surface, and a glucose sensor comprising this enzyme electrode. A carbon electrode, a gold electrode, a platinum electrode, or the like is used as the electrode. The enzyme of the present invention is immobilized on this electrode using carbon. These electrodes may be an electrode prepared by screen printing or the like as the carbon electrode, and an electrode prepared by sputtering as the gold or platinum electrode. The immobilization method may be, for example, a method using a cross-linking reagent, a method involving inclusion in a polymer matrix, a method involving coating with a dialysis membrane, or a method using a photocrosslinkable polymer, a conductive polymer, a redox polymer, or the like. Alternatively, the FAD-GDH according to the present invention may be fixed in a polymer or adsorptively immobilized on the electrode, together with an electron mediator typified by ferrocene or its derivative. These methods may be used in combination. Typically, the FAD-GDH of the present invention is immobilized onto a carbon electrode using glutaraldehyde, and the glutaraldehyde is then blocked by treatment with a reagent having an amine group.

The glucose concentration can be measured as follows: a buffer solution is placed in a thermostated cell, to which a mediator is then added. The cell is kept at a constant temperature. Potassium ferricyanide, phenazine methosulfate, a ruthenium complex, or the like can be used as the mediator. The electrode with the immobilized FAD-GDH of the present invention is used as a working electrode, and a counter electrode (e.g., a platinum electrode) and an optional reference electrode (e.g., an Ag/AgCl electrode) are used. Constant voltage is applied to the carbon electrode to render the current steady. Then, a sample containing glucose is added to the cell, and increase in the current is measured. The glucose concentration in the sample can be calculated according to a calibration curve prepared from a glucose solution having a standard concentration.

The FAD-GDH of the present invention is particularly useful for use in an assay apparatus for blood sugar levels. The assay apparatus can be structurally similar to a commercially available general amperometric biosensor test strip for blood sugar level measurement. As an example, the assay apparatus has two electrodes (working electrode and reference electrode) mounted on an insulator, a reagent port, and a sample receiver. The FAD-GDH of the present invention and a mediator are placed in the reagent port. A sample such as a blood sample is added to the sample receiver to cause the reaction of glucose contained in the sample with the FAD-GDH, resulting in the generation of current. The blood glucose concentration (blood sugar level) can be determined from the value of this current. In addition to electrochemical detection, glucose can also be measured using an optical sensor.

When used herein, an aspect represented by the term "comprising" encompasses an aspect represented by the term "essentially consisting of" and an aspect represented by the term "consisting of".

The contents of all patents and references explicitly cited herein are incorporated herein by reference in their entirety.

EXAMPLES

Hereinafter, the present invention will be described in detail with reference to Examples. However, the present invention is not intended to be limited by these Examples.

Example 1

Preparation of Recombinant Genes of *Sclerotinia sclerotiorum*-Derived Glucose Dehydrogenase (Ssc) and *Aspergillus niger*-Derived Glucose Dehydrogenase (Ang)

The amino acid sequence of *Sclerotinia sclerotiorum*-derived glucose dehydrogenase is shown in SEQ ID NO: 1. A region from the N terminus to the 16th residue can be predicted to be a signal peptide. For example, a free access server SignalP 3.0 Server (http://www.cbs.dtu.dk/services/SignalP-3.0/) can be exploited as a method for predicting a signal sequence cleavage site. This server is run by The Center for Biological Sequence Analysis at the Technical University of Denmark. On the basis of the methodology described in the following literature, an arbitrary amino acid sequence can be searched for the possible presence of a signal sequence to predict its cleavage site: Identification of prokaryotic and eukaryotic signal peptides and prediction of their cleavage sites. Henrik Nielsen, Jacob Engelbrecht, Soren Brunak and Gunnar von Heijne. Protein Engineering, 10:1-6, 1997. According to the prediction using SignalP 3.0

Server, the region from the N terminus to the 16th residue was predicted to be a signal peptide. A gene sequence having codons that encoded an amino acid sequence having the sequence with Ser at position 17 substituted by Met downstream of the initiating methionine and were suitable for recombinant production by E. coli was therefore designed and totally synthesized (Ssc-n1). Also, a gene sequence having codons that encoded an amino acid sequence having the sequence with 23 residues removed from the N-terminal sequence and Met-Thr-Asp-Ser-Thr-Leu-Asn added thereto and were suitable for recombinant production by E. coli was designed and totally synthesized (Ssc-n2). Further, a gene sequence having codons that encoded an amino acid sequence having the sequence with 23 residues removed from the N-terminal sequence and Met-Asn-Thr-Thr-Thr- added thereto and were suitable for recombinant production by E. coli was designed and totally synthesized (Ssc-n3). Further, a gene sequence having codons that encoded an amino acid sequence having the sequence with 23 residues removed from the N-terminal sequence and Met-Ala-Pro-Glu- added thereto and were suitable for recombinant production by E. coli was designed and totally synthesized (Ssc-n4).

The amino acid sequence of *Aspergillus niger*-derived glucose dehydrogenase (Ang) is shown in SEQ ID NO: 2. A region from the N terminus to the 20th residue can be predicted to be a signal peptide in the same way as in the above prediction. According to the prediction using SignalP 3.0 Server, the region from the N terminus to the 20th residue was predicted to be a signal peptide. A gene sequence having codons that encoded an amino acid sequence having the sequence with Ala at position 21 substituted by Met downstream of the initiating methionine and were suitable for recombinant production by E. coli was therefore designed and totally synthesized (Ang-n1). Also, a gene sequence having codons that encoded an amino acid sequence having the sequence with 26 residues removed from the N-terminal sequence and Met-Thr-Asp-Ser-Thr-Leu-Asn added thereto and were suitable for recombinant production by E. coli was designed and totally synthesized (Ang-n2). Further, a gene sequence having codons that encoded an amino acid sequence having the sequence with 26 residues removed from the N-terminal sequence and Met-Asn-Thr-Thr-Thr- added thereto and were suitable for recombinant production by E. coli was designed and totally synthesized (Ang-n3).

The host used for recombinant production was E. coli BL21 (DE3) [F-, ompT, hsdSB(rB- mB-), gal(λcI 857, ind1, Sam7, nin5, lacUV5-T7gene1), dcm(DE3); Novagen/Merck KGaA]. The gene expression vector used was pET30c [kan, lacI; Novagen/Merck KGaA]. The vector for chaperone coexpression used was pGro7 [GroEL, GroES; Takara Bio Inc.].

Example 2

Measurement of Enzymatic Activity

The glucose dehydrogenase activity of the FAD-GDH of the present invention was measured by the quantification of the color degradation of DCIP (2,2'-dichlorodiisopropyl ether) reduced through the reaction of the dehydrogenase with a substrate, on the basis of time-dependent change in absorbance at 600 nm. The reaction conditions were as follows, unless otherwise specified: a substrate was added to a reaction solution (10 mM potassium phosphate (pH 7.0)+ 0.6 mM PMS+0.06 mM DCIP; all the concentrations are final concentrations) containing the enzyme solution to start the reaction, followed by the measurement of change in absorbance at 600 nm. The substrate used was 50 mM (final concentration) glucose. When the amount of the enzyme reducing 1 μmol of DCIP is defined as 1 unit, the value of activity was calculated according to the expression shown below. The molar absorbance coefficient of DCIP at pH 7.0 is defined as 16.3 mM-1 cm-1.

Unit/ml=ΔABS/min×1/16.3×10

The glucose-oxidizing activity of the FAD-GDH of the present invention was measured by the formation of hydrogen peroxide through the reaction of the dehydrogenase with a substrate and the subsequent measurement of time-dependent change in the absorbance at 546 nm of a dye generated using peroxidase, a Trinder reagent (TODB), and 4-aminoantipyrine. The reaction conditions were as follows, unless otherwise specified: a substrate was added to a reaction solution (10 mM potassium phosphate (pH 7.0)+1.5 mM 4-aminoantipyrine+1.5 mM TODB+2 U/ml peroxidase; all the concentrations are final concentrations) containing the enzyme solution to start the reaction, followed by the measurement of change in absorbance at 546 nm. The substrate used was 50 mM (final concentration) glucose. The amount of the enzyme forming 1 μmol of hydrogen peroxide for 1 minute is defined as 1 unit. The molar absorbance constant of TODB at pH 7.0 is defined as 38 mM-1 cm-1. The value of activity is calculated from change in absorbance according to the following expressions:

Unit/ml=ΔABS/min×2/38×10

Unit/mg=Unit/ml/Protein mg/ml

Example 3

Production of GDH Using Medium A and Preparation of Crude Enzyme Preparation

Ssc, Ang, or their enzyme variants were produced using a medium A. E. coli BL21 (DE3) was transformed with an expression vector pET30c having an insert of the gene encoding Ssc, Ang, or each of their enzyme variants. 3 mL of the obtained transformant BL21 (DE3)/pET30c (GDH) was inoculated to an LB medium and shake-cultured overnight at 37° C. Then, 1 ml of the preculture solution was inoculated to 100 mL of the following medium A (50 μg/mL Km) and shake-cultured at 120 rpm at 20° C. using a Sakaguchi flask.

Medium A: LB medium+0.5% glycerol, 0.05% glucose, 0.2% α-lactose, 25 mM (NH4)2SO4, 100 mM KH2PO4, 100 mM NaHPO4, and 1 mM MgSO4 (ZYP medium; modified from F. William Studier et. al., Protein Expression and Purification (2005)).

During the culture, 300 μl of the culture solution was recovered at appropriate time intervals. To the collected bacterial cells, 60 μl of BugBuster Reagent was added, and the mixture was shaken at 4° C. for 20 minutes to lyse the bacterial cells. To the lysate, 60 μl of 10 mM potassium phosphate was added, and a supernatant was recovered by centrifugation (16,000×g, 4° C., 20 minutes). The supernatant was used as a crude enzyme preparation to measure its activity.

Ssc, Ang, or their enzyme variants were expressed as a water-soluble enzyme having GDH activity. As a result of measuring the enzymatic activity of the crude enzyme preparations of Ssc, Ang, or their enzyme variants obtained by culture in the medium A, only the glucose dehydrogenase activity was confirmed, whereas no glucose oxidase activity was detected.

Example 4

Evaluation of Substrate Specificity

Each enzyme obtained using the medium A in Example 3 was assayed for its substrate specificity with glucose, maltose, xylose, and galactose as substrates. As a result, Ssc, Ang, or their enzyme variants had no detectable dehydrogenase activity against maltose or galactose and approximately 10% dehydrogenase activity against xylose, compared with dehydrogenase activity against glucose defined as 100% at a substrate concentration of 5 mM. Under the same conditions as above, previously reported FAD-GDH had 21% dehydrogenase activity against xylose, compared with dehydrogenase activity against glucose defined as 100%. These results demonstrated that Ssc, Ang, or their enzyme variants have lower enzymatic activity against xylose than that of previously reported GDH.

Example 5

Mutagenesis of Ssc and Ang

Site-directed mutagenesis was performed by the QuikChange (registered trademark) method. In the QuikChange (registered trademark) method, each gene prepared in Example 1 was amplified as a template by PCR using primers for mutagenesis. Subsequently, DpnI was added to the sample after PCR, and only the template DNA was digested by incubation at 37° C. for 60 minutes. E. coli DH5α was transformed with the resulting sample. After overnight culture in an LB agar medium (50 μg/ml kanamycin), a plasmid was extracted from an arbitrarily selected clone and confirmed by sequencing to have the introduced mutation of interest. The obtained PCR fragment was digested with NdeI and HindIII (37° C., 2 hours) and ligated with pET30c digested with these restriction enzymes. E. coli BL21 (DE3) was transformed with the resulting sample. After overnight culture in an LB agar medium (50 μg/ml kanamycin), a plasmid was extracted from an arbitrarily selected clone and confirmed by sequencing to have the introduced mutation.

In this way, transformants expressing the following mutated enzymes of Ssc were obtained:
mutated enzymes having S529G, N191X (wherein X represents K, S, R, or E), or G69X (wherein X represents A, H, N, C, D, F, K, L, M, N, or R).

In addition, (multiple-)mutated enzymes were constructed to have one or more mutations selected from the group consisting of Y70F or Y70M, G71S, A73X (wherein X represents E, P, M, T or C), M112C or M112L, A113F or A113S, Y521F, S523P, F525W or F525Y, P527X (wherein X represents M, I, Q, V, or Y), A182R, S505P, V571C, N46E, N240E, N274E, N275K, and N370K or N370E. Also, multiple-mutated enzymes were constructed to have N191K/S529G, N191S/S529G, N191R/S529G, or N191E/S529G. Multiple mutated enzymes were further constructed to have N191K/S529G/G69X (wherein X represents A, H, N, C, D, F, K, L, M, N, or R), N191K/S529G/Y70F, N191K/S529G/F525Y, N191K/S529G/P527Y, N191K/S529G/P527V, N191K/S529G/P527Y, N191K/S529G/F525Y/P527Y, N191K/S529G/F525Y/P527Y/G69A, or N191K/S529G/S505P. Multiple-mutated enzymes were further constructed to have N191K/S529G/S505P/N46E, N191K/S529G/S505P/N240E, N191K/S529G/S505P/N274E, N191K/S529G/S505P/N275E, N191K/S529G/S505P/N370K, or N191K/S529G/S505P/N370E.

Also, transformants expressing the following mutated enzymes of Ang were obtained:
(multiple-)mutated enzymes having N368K, T522S, E195K, Q196X (wherein X represents E, D, or R), N368K/T522S, E195K/Q196X (wherein X represents E, D, or R), N368K/T522S/E195K/Q196E, E195K/Q196E/G73A, E195K/Q196E/S75G, E195K/Q196E/G73A/S75G, E195K/Q196E/S69E/N70D/G73A, E195K/Q196E/Y524F, E195K/Q196E/P526X (wherein X represents G, V, I, F, Y, S, T, C, M, H, or Q), E195K/Q196E/G73A/Y524F, E195K/Q196E/G73A/P526X (wherein X represents I, F, S, or M), E195K/Q196E/G73A/S75G/Y524F, E195K/Q196E/G73A/S75G/P526X (wherein X represents I, F, Y, S, or M), N368K/T522S, or N368K/T522S/E195K/Q196E.

Example 6

Production of Mutated Enzyme and Measurement of Activity

The transformant BL21 (DE3) expressing each mutated enzyme was precultured. The transformant was inoculated in an amount of 1% with respect to 60 ml of a medium A using a 300-ml baffled flask and shake-cultured under conditions involving 20° C., 28 hours, and 125 rpm. After collection of 50 ml of the medium, the bacterial cells were suspended by the addition of BugBuster (registered trademark) protein extraction reagent (Novagen/Merck KGaA) at a ratio of 5 ml per g of wet cells and incubated at room temperature for 15 minutes with gentle shaking. Insoluble fractions were removed by centrifugation (15 Krpm, 4° C., 20 minutes). Then, the obtained supernatant was dialyzed overnight at 4° C. against a 20 mM potassium phosphate buffer solution (pH 6.5). After the completion of the dialysis, the dialysate was centrifuged, and the supernatant was used as a crude enzyme preparation. Insoluble fractions were suspended in a 20 mM potassium phosphate buffer solution (pH 6.5) at a ratio of 1 ml per 2 ml of the suspension containing the insoluble fractions.

A small-scale expression system was used for some multiple-mutated enzymes. The transformant BL21 (DE3) expressing each mutated enzyme was precultured, and the transformant was inoculated in an amount of 1 vol % with respect to 3 ml of a medium A. The bacterial cells were shake-cultured at 37° C. for 4 hours and then shake-cultured at 20° C. for 20 hours. After the culture, 2 ml of the medium was collected, then suspended by the addition of 400 μl of BugBuster (registered trademark), and then shaken at room temperature for 15 minutes. Then, the suspension was centrifuged (15000 rpm, 4° C., 20 minutes), and the obtained supernatant was used as a crude enzyme preparation.

The GDH activity was measured in a DCIP (0.3 mM)/PMS (0.6 mM) system using a 20 mM potassium phosphate buffer solution (pH 6.5) as a buffer solution and glucose (Glc; 1, 2, 4, 10, 20, and 40 mM) and xylose (Xyl; 4 and 40 mM) as substrates.

Also, the thermal stability was tested as follows: 200 μl of the crude enzyme preparation was added to 800 μl of a 20 mM potassium phosphate buffer solution (pH 6.5) preheated to 45° C., followed by mixing. Immediately thereafter, 100 μl of the mixture was added (final concentration: 10-fold dilution) to 100 μl of a 20 mM potassium phosphate buffer solution (pH 6.5) preheated to 45° C. After the addition, the mixture was incubated at 45° C. for 2, 5, 10, 15, 20, 25, or 30 minutes. Immediately after a lapse of the given time, the mixture was cooled in ice. The GDH activity was measured in a DCIP (0.3 mM)/PMS (0.6 mM) system using a 20 mM potassium phosphate buffer solution (pH 6.5) as a buffer solution and Glc (40 mM) as a substrate.

The results of evaluating the mutated enzymes of Ssc are shown in Tables 1 to 6. The numeric values in the tables represent a mean of several data about specific activity (U/mg) and productivity (U/L) obtained under the same conditions with 40 mM glucose as a substrate. The obtained crude enzyme preparation was used to observe the correlation between the concentration of the substrate (glucose; 1, 2, 4, 10, 20, and 40 mM) and the activity. The obtained Michaelis-Menten constant (Km value) and apparent maximum activity (Vmax) were determined from a saturation curve determined therefrom.

TABLE 1

|  | U/mg | U/L medium | Xyl/Glc 4 mM/4 mM (%) | Xyl/Glc 40 mM/40 mM (%) | Km (mM) | Vmax (U/mg protein) | Vmax/Km |
| --- | --- | --- | --- | --- | --- | --- | --- |
| Ssc-n1 (WT) | 0.50 | 358 | 13.8 | 10.6 | 16.6 | 0.7 | 0.04 |
| Ssc-n1 S529G | 2.47 | 1,673 | 8.9 | 11.4 | 17.3 | 3.6 | 0.21 |
| Ssc-n1 N191K | 1.15 | 735 | 9.0 | 10.3 | 16.0 | 1.6 | 0.10 |
| Ssc-n1 N191S | 2.60 | 1,516 | 8.1 | 10.1 | 16.6 | 3.7 | 0.22 |
| Ssc-n1 N191R | 3.91 | 2,245 | 7.4 | 10.1 | 16.1 | 5.6 | 0.35 |
| Ssc-n1 N191E | 3.80 | 1,967 | 8.1 | 10.7 | 18.4 | 5.6 | 0.31 |
| Ssc-n1 N191K/S529G | 4.90 | 3,409 | 9.3 | 14.5 | 16.9 | 7.2 | 0.43 |

Table 1 shows the results of evaluating the mutated enzymes of Ssc-n1 in 60 ml of cultures. The mutated enzymes having the substitution N191K, N191S, N191R, or N191E all exhibited improved productivity of 2 times for N191K (735 U/L), 4.2 times for N191S (1516 U/L), 6.3 times for N191R (2245 U/L), and 5.5 times for N191E (1967 U/L), compared with the enzyme having wild-type N191 (358 U/L). The mutated enzyme having the substitution S529G (1673 U/L) had 4.7 times the productivity of the wild type. Among others, the combination of these mutations succeeded in drastic improvement in productivity (Ssc-n1 N191K/S529G (3409 U/L)), which was 9.5 times the productivity of the wild type.

TABLE 2

|  | U/mg | U/L medium | Xyl/Glc 4 mM/4 mM (%) | Xyl/Glc 40 mM/40 mM (%) | Km (mM) | Vmax (U/mg protein) | Vmax/Km |
| --- | --- | --- | --- | --- | --- | --- | --- |
| Ssc-n2 | 4.02 | 2,402 | 8.0 | 10.4 | 17.0 | 5.9 | 0.34 |
| Ssc-n2 N191K/S529G | 25.45 | 17,594 | 10.5 | 12.9 | 19.3 | 38.2 | 1.98 |
| Ssc-n2 N191S/S529G | 14.07 | 9,325 | 10.2 | 13.5 | 14.4 | 19.4 | 1.35 |
| Ssc-n2 N191R/S529G | 9.66 | 7,271 | 9.4 | 11.5 | 24.2 | 15.7 | 0.65 |
| Ssc-n2 N191E/S529G | 13.44 | 9,505 | 10.4 | 12.0 | 20.7 | 20.2 | 0.98 |
| Ssc-n1 N191K/S529G | 4.90 | 3,409 | 9.3 | 14.5 | 16.9 | 7.2 | 0.43 |
| Ssc-n3 | 1.28 | 716 | 10.5 | 10.0 | 19.0 | 1.9 | 0.10 |
| Ssc-n3 N191K/S529G | 4.77 | 3,124 | 10.7 | 14.0 | 17.4 | 6.9 | 0.40 |
| Ssc-n4 | 4.01 | 1,952 | 8.2 | 9.5 | 17.3 | 5.8 | 0.33 |
| Ssc-n4 N191K/S529G | 6.66 | 3,918 | 10.3 | 12.6 | 15.4 | 9.2 | 0.60 |

Table 2 shows the results of evaluating double mutations using Ssc-n2, -n3, and -n4 in 60 ml of cultures. The double-mutated enzymes of Ssc-n2, -n3, and -n4 having N191K/S529G all exhibited improved productivity compared with wild-type Ssc-n1 and also exhibited higher productivity than that of Ssc-n2, -n3, and -n4, respectively. The double-mutated enzymes of Ssc-n2 having S529G in combination with N191S, N191R, or N191E also exhibited improved productivity compared with Ssc-n2 and wild-type Ssc-n1. These results demonstrated that the double mutation N191K/S529G is a very effective mutation for improvement in the productivity of Ssc.

TABLE 3

|  | U/mg | U/L medium | Xyl/Glc 4 mM/4 mM (%) | Xyl/Glc 40 mM/40 mM (%) | Km (mM) | Vmax (U/mg protein) | Vmax/Km |
| --- | --- | --- | --- | --- | --- | --- | --- |
| Ssc-n1 | 0.50 | 358 | 13.8 | 10.6 | 16.6 | 0.7 | 0.04 |
| Ssc-n2 | 4.02 | 2,402 | 8.0 | 10.4 | 17.0 | 5.9 | 0.34 |
| Ssc-n1 N191K/S529G | 4.90 | 3,409 | 9.3 | 14.5 | 16.9 | 7.2 | 0.43 |
| Ssc-n2 N191K/S529G | 25.45 | 17,594 | 10.5 | 12.9 | 19.3 | 38.2 | 1.98 |
| Ssc-n2 N191K/S529G/G69A | 15.62 | 8,861 | 5.8 | 5.7 | 27.8 | 26.4 | 0.95 |
| Ssc-n2 N191K/S529G/G69H | 3.41 | 2,353 | 5.1 | 4.5 | 40.8 | 6.9 | 0.17 |
| Ssc-n2 N191K/S529G/G69N | 8.22 | 5,123 | 5.7 | 4.8 | 26.0 | 13.9 | 0.53 |
| Ssc-n2 N191K/S529G/Y70F | 8.92 | 5,404 | 7.6 | 7.0 | 65.2 | 23.8 | 0.37 |
| Ssc-n2 N191K/S529G/A73E | 2.64 | 1,473 | 5.3 | 5.7 | 25.4 | 4.3 | 0.17 |
| Ssc-n2 N191K/S529G/A73P | 4.13 | 2,210 | 7.3 | 8.2 | 22.3 | 6.5 | 0.29 |

Table 3 shows the results of evaluating the combinations of N191K/S529G with a mutation G69A (or G69H or G69N), Y70F, or A73E (or A73P) using Ssc-n2 in 60 ml of cultures. All the mutations improved productivity compared with wild-type Ssc-n1. All the combinations except for A73E and G69H improved productivity compared with Ssc-n2. In addition, all the mutated enzymes had approximately 5 to 7% reactivity with xylose relative to their activity against glucose with the same concentration thereas. Thus, the mutated enzymes had much higher specificity for glucose and lower activity against xylose, compared with the wild-type.

bination with various mutations in 3 ml of cultures. In this context, the reference activity is that of wild-type Ssc-n1. All the multiple-mutated enzymes had values exceeding this reference activity, showing that all the mutations are effective for improvement in productivity. When compared with the evaluation results about 60 ml of Ssc-n2, the combined mutations except for A73M, M112C, and A113F achieved higher productivity than that of Ssc-n2, showing that the combinations of N191K/S529G with various mutations are effective for improvement in productivity. Among them, particularly, N191K/S529G/F525Y, N191K/S529G/P527Y,

TABLE 4

|  | U/mg | U/L medium | Xyl/Glc 4 mM/4 mM (%) | Xyl/Glc 40 mM/40 mM (%) | Km (mM) | Vmax (U/mg protein) | Vmax/Km |
|---|---|---|---|---|---|---|---|
| Ssc-n1 | 1.63 | 1,061 | 9.3 | 12.2 | 14.3 | 2.2 | 0.15 |
| Ssc-n2 <60 ml> | 4.02 | 2,402 | 8.0 | 10.4 | 17.0 | 5.9 | 0.34 |
| Ssc-n2 N191K/S529G <60 ml> | 25.45 | 17,594 | 10.5 | 12.9 | 19.3 | 38.2 | 1.98 |
| Ssc-n2 N191K/S529G | 13.0 | 9,405 | 10.5 | 16.7 | 12.5 | 16.9 | 1.35 |
| Ssc-n2 N191K/S529G/G69A | 10.58 | 9,411 | 6.9 | 7.5 | 17.5 | 15.8 | 0.90 |
| Ssc-n2 N191K/S529G/G69C | 4.67 | 4,974 | 6.6 | 4.9 | 39.7 | 9.3 | 0.23 |
| Ssc-n2 N191K/S529G/G69D | 4.48 | 4,159 | 7.1 | 4.9 | 48.0 | 9.7 | 0.20 |
| Ssc-n2 N191K/S529G/G69F | 4.36 | 4,009 | 7.4 | 5.6 | 23.9 | 7.0 | 0.29 |
| Ssc-n2 N191K/S529G/G69H | 7.38 | 6,280 | 6.3 | 5.5 | 22.1 | 11.1 | 0.50 |
| Ssc-n2 N191K/S529G/G69K | 5.42 | 4,569 | 7.8 | 5.2 | 38.4 | 10.7 | 0.28 |
| Ssc-n2 N191K/S529G/G69L | 4.34 | 3,762 | 7.5 | 4.7 | 37.2 | 8.5 | 0.23 |
| Ssc-n2 N191K/S529G/G69M | 5.69 | 5,048 | 6.8 | 4.8 | 47.8 | 12.4 | 0.26 |
| Ssc-n2 N191K/S529G/G69N | 7.23 | 6,103 | 6.2 | 5.9 | 23.5 | 11.5 | 0.49 |
| Ssc-n2 N191K/S529G/G69R | 5.25 | 4,349 | 6.7 | 5.5 | 22.8 | 8.0 | 0.35 |
| Ssc-n2 N191K/S529G/Y70F | 5.18 | 4,052 | 6.8 | 8.1 | 29.7 | 9.0 | 0.30 |
| Ssc-n2 N191K/S529G/Y70M | 2.99 | 2,725 | 11.8 | 10.8 | 40.4 | 6.2 | 0.15 |
| Ssc-n2 N191K/S529G/G71S | 696 | 3,267 | 6.8 | 11.2 | 13.0 | 7.3 | 0.56 |
| Ssc-n2 N191K/S529G/A73M | 3.20 | 1,964 | 7.8 | 6.7 | 23.9 | 5.2 | 0.22 |
| Ssc-n2 N191K/S529G/A73P | 4.51 | 3,526 | 7.4 | 9.3 | 16.0 | 6.2 | 0.39 |
| Ssc-n2 N191K/S529G/A73T | 6.75 | 4,567 | 8.1 | 9.3 | 14.8 | 9.4 | 0.63 |
| Ssc-n2 N191K/S529G/A73C | 6.83 | 5,692 | 8.4 | 12.7 | 13.4 | 9.2 | 0.68 |
| Ssc-n2 N191K/S529G/M112C | 2.62 | 1,688 | 11.4 | 8.9 | 26.7 | 4.3 | 0.16 |
| Ssc-n2 N191K/S529G/M112L | 3.70 | 2,744 | 10.3 | 10.1 | 17.2 | 69 | 0.31 |
| Ssc-n2 N191K/S529G/A113F | 2.65 | 2,105 | 9.5 | 8.8 | 30.5 | 4.7 | 0.15 |
| Ssc-n2 N191K/S529G/A113S | 4.30 | 3,402 | 8.7 | 8.7 | 25.5 | 7.0 | 0.27 |
| Ssc-n2 N191K/S529G/Y521F | 5.99 | 4,521 | 9.0 | 10.7 | 19.9 | 8.9 | 0.45 |
| Ssc-n2 N191K/S529G/S523P | 5.88 | 4,648 | 11.7 | 12.5 | 18.1 | 8.6 | 0.47 |
| Ssc-n2 N191K/S529G/F525W | 4.98 | 3,339 | 23.2 | 24.7 | 3.3 | 5.4 | 1.65 |
| Ssc-n2 N191K/S529G/F525Y | 16.71 | 13,001 | 9.2 | 14.8 | 13.8 | 21.4 | 1.55 |
| Ssc-n2 N191K/S529G/P527Q | 3.79 | 2,524 | 11.8 | 7.0 | 87.7 | 12.0 | 0.14 |
| Ssc-n2 N191K/S529G/P527M | 4.74 | 3,336 | 11.5 | 8.0 | 67.9 | 12.6 | 0.19 |
| Ssc-n2 N191K/S529G/P527I | 8.00 | 5,882 | 8.5 | 9.8 | 33.7 | 14.6 | 0.43 |
| Ssc-n2 N191K/S529G/P527V | 12.40 | 8,509 | 8.8 | 13.1 | 31.3 | 22.2 | 0.71 |
| Ssc-n2 N191K/S529G/P527Y | 21.51 | 16,843 | 7.1 | 11.2 | 28.7 | 36.0 | 1.25 |
| Ssc-n2 N191K/S529G/F525Y/P527Y | 18.29 | 21,024 | 6.4 | 11.0 | 28.5 | 29.8 | 1.04 |
| Ssc-n2 N191K/S529G/G69A/F525Y/P527Y | 4.75 | 6988 | 6.7 | 6.4 | 24.1 | 4.5 | 0.18 |

Table 4 shows the results of evaluating the multiple-mutated enzymes of Ssc-n2 having N191K/S529G in comand N191K/F525Y/S529G/P527Y achieved very high productivity.

TABLE 5

|  | U/mg | U/L medium | Xyl/Glc 4 mM/4 mM (%) | Xyl/Glc 40 mM/40 mM (%) | Km (mM) | Vmax (U/mg protein) | Vmax/Km |
|---|---|---|---|---|---|---|---|
| Ssc-n1 | 0.50 | 358 | 13.8 | 10.6 | 16.6 | 0.7 | 0.04 |
| Ssc-n2 | 4.02 | 2,402 | 8.0 | 10.4 | 17.0 | 5.9 | 0.34 |
| Ssc-n1 N191K/S529G | 4.90 | 3,409 | 9.3 | 14.5 | 16.9 | 7.2 | 0.43 |
| Ssc-n2 N191K/S529G | 25.45 | 17,594 | 10.5 | 12.9 | 19.3 | 38.2 | 1.98 |
| Ssc-n2 N191K/S529G/F525W | 10.19 | 5,572 | 26.9 | 24.6 | 3.6 | 11.4 | 3.16 |
| Ssc-n2 N191K/S529G/F525Y | 30.01 | 17,806 | 11.0 | 13.2 | 21.1 | 47.2 | 2.23 |
| Ssc-n2 N191K/S529G/P527V | 19.16 | 10,092 | 10.6 | 10.8 | 116.2 | 75.2 | 0.65 |
| Ssc-n2 N191K/S529G/P527Y | 36.40 | 24,918 | 9.0 | 8.1 | 73.3 | 103.1 | 1.41 |

Table 5 shows the results of evaluating the multiple-mutated enzymes of Ssc-n2 having N191K/S529G in combination with a mutation F525W, F525Y, P527V, or P527Y in 60 ml of cultures. All the multiple-mutated enzymes had values exceeding the productivity of Ssc-n1 and Ssc-n2. N191K/S525G/P527Y yielded a value exceeding productivity brought about by N191K/S525G. Thus, these mutated enzymes were shown to be excellent.

particularly, N191K/S529G/S505P yielded excellent productivity. These mutations were also found to include a mutation improving thermal stability.

The results of evaluating the mutated enzymes of Ang are shown in Tables 7 and 8. The numeric values in the tables represent a mean of several data about specific activity (U/mg) and productivity (U/L) obtained under the same conditions with 40 mM glucose as a substrate. The obtained

TABLE 6

| | U/mg | U/L medium | Remaining activity 45° C.-10 min (%) | Xyl/Glc 4 mM/4 mM (%) | Xyl/Glc 40 mM/40 mM (%) | Km (mM) | Vmax (U/mg protein) | Vmax/Km |
|---|---|---|---|---|---|---|---|---|
| Ssc-n1 | 1.63 | 1,061 | 0.2 | 9.3 | 12.2 | 14.3 | 2.2 | 0.15 |
| Ssc-n2 <60 ml> | 4.02 | 2,402 | nt | 8.0 | 10.4 | 17.0 | 5.9 | 0.34 |
| Ssc-n2 N191K/S529G <60 ml> | 25.45 | 17,594 | nt | 10.5 | 12.9 | 19.3 | 38.2 | 1.98 |
| Ssc-n2 N191K/S529G | 13.00 | 9,405 | 0.6 | 10.5 | 16.7 | 12.5 | 16.9 | 1.35 |
| Ssc-n2 N191K/S529G/A182R | 11.71 | 7,529 | 4.7 | 13.4 | 16.2 | 13.4 | 14.3 | 1.07 |
| Ssc-n2 N191K/S529G/S505P | 19.37 | 15,947 | 0.9 | 12.3 | 15.2 | 12.1 | 23.4 | 1.93 |
| Ssc-n2 N191K/S529G/V571C | 9.42 | 6,364 | 13.8 | 14.4 | 12.3 | 9.4 | 5.8 | 0.62 |
| Ssc-n2 N191K/S529G/S505P/N46E | 10.24 | 7,129 | 1.4 | 11.2 | 17.2 | 9.1 | 12.6 | 1.40 |
| Ssc-n2 N191K/S529G/S505P/N240E | 18.47 | 13,244 | 1.9 | 10.7 | 18.5 | 10.4 | 23.3 | 2.24 |
| Ssc-n2 N191K/S529G/S505P/N274E | 11.93 | 9,316 | 1.3 | 11.4 | 16.1 | 14.1 | 15.1 | 1.07 |
| Ssc-n2 N191K/S529G/S505P/N275K | 8.41 | 5,989 | 2.1 | 11.7 | 16.4 | 13.6 | 11.2 | 0.83 |
| Ssc-n2 N191K/S529G/S505P/N370K | 7.79 | 5,559 | 1.2 | 11.7 | 21.3 | 6.9 | 9.5 | 1.38 |
| Ssc-n2 N191K/S529G/S505P/N370E | 9.99 | 8,671 | 1.2 | 11.9 | 16.8 | 12.2 | 12.6 | 1.04 |

Table 6 shows the results of evaluating the multiple-mutated enzymes of Ssc-n2 having N191K/S529G in combination with various mutations in 3 ml of cultures. All the multiple-mutated enzymes had values exceeding the productivity of Ssc-n1 and Ssc-n2, showing that the combinations of these mutations improve productivity. Among them, crude enzyme preparation was used to observe the correlation between the concentration of the substrate (glucose; 1, 2, 4, 10, 20, and 40 mM) and the activity. The obtained Michaelis-Menten constant (Km value) and apparent maximum activity (Vmax) were determined from a saturation curve determined therefrom.

TABLE 7

| | U/mg | U/Lmedium | Xyl/Glc 4 mM/4 mM (%) | Xyl/Glc 40 mM/40 mM (%) | Km (mM) | Vmax (U/mg protein) | Vmax/Km |
|---|---|---|---|---|---|---|---|
| Ang-n1 | 0.16 | 84 | 5.0 | 7.2 | 3.6 | 0.2 | 0.05 |
| Ang-n1 E195K/Q196E | 2.39 | 1,199 | 4.0 | 9.5 | 2.8 | 2.5 | 0.90 |
| Ang-n2 | 1.45 | 775 | 3.9 | 11.4 | 3.0 | 1.5 | 0.51 |
| Ang-n2 N368K | 0.66 | 413 | 5.0 | 10.0 | 4.6 | 0.7 | 0.16 |
| Ang-n2 T522S | 3.20 | 1,876 | 10.9 | 26.9 | 2.5 | 3.4 | 1.36 |
| Ang-n2 N368K/T522S | 5.03 | 3,076 | 10.6 | 26.7 | 3.4 | 5.3 | 1.54 |
| Ang-n2 E195K/Q196E | 6.17 | 3,738 | 4.3 | 10.6 | 2.1 | 6.5 | 3.13 |
| Ang-n2 E195K/Q196D | 4.95 | 3,020 | 4.5 | 12.8 | 2.9 | 5.1 | 1.80 |
| Ang-n2 E195K/Q196R | 4.20 | 2,769 | 4.6 | 12.6 | 2.5 | 4.3 | 1.77 |
| Ang-n2 E195K/Q196E/N368K/T522S | 5.67 | 3,660 | 10.3 | 23.8 | 3.2 | 6.1 | 1.93 |
| Ang-n3 | 0.58 | 295 | 6.0 | 8.7 | 3.7 | 0.7 | 0.18 |
| Ang-n3 E195K/Q196E | 4.28 | 2,564 | 4.5 | 10.6 | 2.2 | 4.5 | 2.02 |

Table 7 shows the results of evaluating the mutated enzymes of Ang-n1, -n2, and -n3 in 60 ml of cultures. All the mutated enzymes exhibited improved productivity compared with wild-type Ang-n1. In the evaluation of the mutated enzymes of Ang-n2, T522S and the double mutation N368K/T522S yielded drastically higher productivity compared with Ang-n1 and Ang-n2. The combinations of Ang-n1, Ang-n2, and Ang-n3 with E195K/Q196E drastically improved productivity. Also, the combinations of Ang-n2 with E195D or R and Q196E were able to achieve drastic improvement in productivity. These results demonstrated that the mutated enzymes prepared using these mutations and combinations thereof are mutated enzymes with improved productivity.

TABLE 8

|  | U/mg | U/L medium | Xyl/Glc 4 mM/ 4 mM (%) | Xyl/Glc 40 mM/ 40 mM (%) | Km (mM) | Vmax (U/mg protein) | Vmax Km |
|---|---|---|---|---|---|---|---|
| Ang-n2 | 1.45 | 775 | 2.9 | 11.4 | 3.0 | 1.5 | 0.51 |
| Ang-n2 E195K/Q196E | 6.49 | 6,046 | 4.5 | 11.8 | 2.7 | 6.9 | 2.58 |
| Ang-n2 E195K/Q196E/G73A | 4.44 | 4,839 | 2.5 | 4.3 | 5.5 | 5.0 | 0.91 |
| Ang-n2 E195K/Q196E/S75G | 11.80 | 8,841 | 6.9 | 19.2 | 1.7 | 12.3 | 7.26 |
| Ang-n2 E195K/Q196E/G73A/S75G | 10.63 | 8,115 | 3.5 | 9.2 | 2.5 | 11.3 | 4.50 |
| Ang-n2 E195K/Q196E/S69E/N70D/G73A | 2.32 | 1,814 | 2.9 | 3.8 | 3.2 | 2.5 | 0.78 |
| Ang-n2 E195K/Q196E/Y524F | 10.12 | 7,424 | 4.4 | 14.6 | 1.7 | 10.5 | 6.09 |
| Ang-n2 E195K/Q196E/P526G | 6.86 | 4,712 | 2.6 | 4.0 | 6.6 | 8.0 | 1.21 |
| Ang-n2 E195K/Q196E/P526V | 6.07 | 4,120 | 3.6 | 10.5 | 0.9 | 6.2 | 6.82 |
| Ang-n2 E195K/Q196E/P526I | 6.11 | 4,565 | 2.5 | 6.9 | 1.8 | 6.4 | 3.57 |
| Ang-n2 E195K/Q196E/P526F | 9.14 | 6,581 | 2.0 | 5.0 | 4.7 | 10.2 | 2.18 |
| Ang-n2 E195K/Q196E/P526Y | 5.17 | 4,098 | 1.6 | 4.4 | 3.6 | 5.6 | 1.58 |
| Ang-n2 E195K/Q196E/P526S | 6.16 | 3,807 | 2.2 | 3.6 | 8.9 | 7.5 | 0.85 |
| Ang-n2 E195K/Q196E/P526T | 6.85 | 4,844 | 2.1 | 4.7 | 5.0 | 7.8 | 1.55 |
| Ang-n2 E195K/Q196E/P526C | 8.85 | 6,528 | 3.0 | 10.0 | 3.1 | 9.3 | 3.00 |
| Ang-n2 E195K/Q196E/P526M | 6.14 | 4,876 | 2.4 | 5.3 | 3.4 | 6.8 | 1.96 |
| Ang-n2 E195K/Q196E/P526H | 2.94 | 2,022 | 2.1 | 2.7 | 9.3 | 3.6 | 0.38 |
| Ang-n2 E195K/Q196E/P526Q | 3.29 | 2,158 | 2.9 | 3.8 | 5.2 | 3.7 | 0.71 |
| Ang-n2 E195K/Q196E/G73A/Y524F | 6.48 | 5,013 | 2.6 | 5.9 | 2.2 | 6.9 | 3.15 |
| Ang-n2 E195K/Q196E/G73A/P526I | 2.99 | 2,135 | 1.8 | 4.1 | 3.3 | 3.3 | 0.98 |
| Ang-n2 E195K/Q196E/G73A/P526F | 2.54 | 1,958 | 2.1 | 4.0 | 5.3 | 2.8 | 0.53 |
| Ang-n2 E195K/Q196E/G73A/P526S | 1.61 | 1,125 | 2.4 | 3.1 | 7.4 | 1.9 | 0.26 |
| Ang-n2 E195K/Q196E/G73A/P526M | 2.72 | 2,010 | 1.6 | 2.6 | 4.8 | 3.1 | 0.64 |
| Ang-n2 E195K/Q196E/G73A/S75G/Y524F | 10.06 | 7,166 | 4.1 | 12.1 | 1.2 | 10.5 | 8.57 |
| Ang-n2 E195K/Q196E/G73A/S75G/P526I | 8.34 | 5,965 | 2.5 | 4.5 | 3.4 | 9.2 | 2.69 |
| Ang-n2 E195K/Q196E/G73A/S75G/P526F | 11.55 | 7,700 | 2.3 | 3.7 | 6.0 | 13.1 | 2.19 |
| Ang-n2 E195K/Q196E/G73A/S75G/P526Y | 7.61 | 5,336 | 1.3 | 2.8 | 7.4 | 9.0 | 1.22 |
| Ang-n2 E195K/Q196E/G73A/S75G/P526S | 8.50 | 6,427 | 1.3 | 2.7 | 13.0 | 11.3 | 0.87 |
| Ang-n2 E195K/Q196E/G73A/S75G/P526M | 9.31 | 6,413 | 1.4 | 3.4 | 6.0 | 10.8 | 1.81 |

Table 8 shows the results of evaluating the combinations of E195K/Q196E with other amino acid mutations using Ang-n2 in 3 ml of cultures. These mutated enzymes exhibited higher productivity than that of Ang-n2, demonstrating these mutations are effective. These mutated enzymes were further found to have reduced activity against xylose. Particularly, E195K/Q196E/G73A and E195K/Q196E/S75G improved productivity. E195K/Q196E/G73A/S75G improved productivity and substrate specificity. E195K/Q196E/S69E/N70D/G73A improved substrate specificity. E195K/Q196E/Y524F improved productivity and Km. E195K/Q196E/P526X improved substrate specificity.

Of them, particularly interesting mutants were cultured at a scale of 60 ml, and the enzymes were purified using acetic acid and evaluated. The results are shown in Table 9. E195K/Q196E/G73A/S75G/P526M improved productivity, Vmax, and substrate specificity.

TABLE 9

|  | U/mg | U/L medium | Xyl/Glc 4 mM/4 mM (%) | Xyl/Glc 40 mM/ 40 mM (%) | Km (mM) | Vmax (U/mg protein) | Vmax/ Km |
|---|---|---|---|---|---|---|---|
| Ang-n2 | 8.84 | 540 | 3.7 | 10.3 | 2.5 | 9.4 | 3.72 |
| Ang-n2 E195K/Q196E | 18.29 | 2,589 | 4.4 | 13.5 | 1.9 | 19.6 | 10.47 |
| Ang-n2 E195K/Q196E/G73A/S75G | 25.41 | 2,832 | 3.2 | 7.4 | 2.3 | 26.0 | 11.24 |
| Ang-n2 E195K/Q196E/G73A/S75G/P526M | 36.42 | 3,704 | 1.6 | 3.2 | 6.0 | 39.1 | 6.55 |

Example 7

Preparation and Evaluation of Enzyme Sensor

Enzyme electrodes were prepared using Ssc-n2N191K/S529G as a mutated enzyme of Ssc and Ang-n2E195K/Q196E as a mutated enzyme of Ang. To 5 units of each FAD-GDH variant of the present invention, 20 mg of carbon paste was added, and the mixture was freeze-dried. The resulting product was well mixed, then applied only to the surface of a carbon paste electrode already charged with approximately 40 mg of a carbon paste, and polished on a filter paper. This electrode was treated at room temperature for 30 minutes in a 10 mM MOPS buffer solution (pH 7.0) containing 1% glutaraldehyde and then treated at room temperature for 20 minutes in a 10 mM MOPS buffer solution (pH 7.0) containing 20 mM lysine to block the glutaraldehyde. This electrode was equilibrated with a 10 mM MOPS buffer solution (pH 7.0) at room temperature for 1 hour or longer. The electrode was stored at 4° C.

The prepared enzyme sensor was used to measure glucose concentrations. The enzyme sensor with the immobilized FAD-GDH variant of the present invention was able to quantify glucose within the range of 0.1 mM to 5 mM.

INDUSTRIAL APPLICABILITY

The present invention is useful in the measurement of glucose concentrations, particularly, the measurement of blood sugar levels.

The invention claimed is:

1. A protein comprising the amino acid sequence set forth in SEQ ID NO: 2 having glucose dehydrogenase activity, wherein the protein has an amino acid mutation E195K, Q196X (wherein X represents E, D, or R), Y524F, P526X (wherein X represents G, V, I, F, Y, S, T, C, M, H, or Q), N368K, or T522S, or a combination thereof.

2. A protein comprising the amino acid sequence set forth in SEQ ID NO: 2 having glucose dehydrogenase activity, wherein the protein has an amino acid mutation selected from the group consisting of E195K/Q196X (wherein X represents E, D, or R), E195K/Q196E/G73A, E195K/Q196E/S75G, E195K/Q196E/G73A/S75G, E195K/Q196E/S69E/N70D/G73A, E195K/Q196E/Y524F, E195K/Q196E/P526X (wherein X represents G, V, I, F, Y, S, T, C, M, H, or Q), E195K/Q196E/G73A/Y524F, E195K/Q196E/G73A/P526X (wherein X represents I, F, S, or M), E195K/Q196E/G73A/S75G/Y524F, E195K/Q196E/G73A/S75G/P526X (wherein X represents I, F, Y, S, or M), N368K/T522S, and N368K/T522S/E195K/Q196E.

3. The protein according to claim 2, wherein the protein has an amino acid mutation selected from the group consisting of E195K/Q196E/G73A/S75G/P526M, E195K/Q196E/Y524F, E195K/Q196E/P526X, E195K/Q196E/S69E/N70D/G73A, E195K/Q196E/G73A/S75G, E195K/Q196E/S75G, and E195K/Q196E/G73A.

4. The protein according to claim 1, wherein in the protein comprising the amino acid sequence set forth in SEQ ID NO: 2, 20 residues are deleted from the N-terminal sequence thereof, and the Ala residue at position 21 is substituted by Met.

5. The protein according to claim 1, wherein in the protein comprising the amino acid sequence set forth in SEQ ID NO: 2, 26 residues are deleted from the N-terminal sequence thereof, and Met-Thr-Asp-Ser-Thr-Leu-Asn or Met-Asn-Thr-Thr-Thr- is added.

6. A protein comprising the amino acid sequence set forth in SEQ ID NO: 1 having glucose dehydrogenase activity, wherein the protein has an amino acid mutation S529G, N191X (wherein X represents K, S, R, or E), or G69X (wherein X represents A, H, N, C, D, F, K, L, M, N, or R), or a combination thereof.

7. The protein according to claim 6, wherein the protein further has one or more mutations selected from the group consisting of Y70F or Y70M, G71S, A73X (wherein X represents E, P, M, T, or C), M112C or M112L, A113F or A113S, Y521F, S523P, F525W or F525Y, P527X (wherein X represents M, I, Q, V, or Y), A182R, S505P, V571C, N46E, N240E, N274E, N275K, and N370K or N370E.

8. A protein comprising the amino acid sequence set forth in SEQ ID NO: 1 having glucose dehydrogenase activity, wherein the protein has an amino acid mutation selected from the group consisting of N191K/S529G, N191S/S529G, N191R/S529G, and N191E/S529G.

9. A protein comprising the amino acid sequence set forth in SEQ ID NO: 1 having glucose dehydrogenase activity, wherein the protein has an amino acid mutation selected from the group consisting of N191K/S529G/G69X (wherein X represents A, H, N, C, D, F, K, L, M, N, or R), N191K/S529G/Y70F, N191K/S529G/F525Y, N191K/S529G/P527Y, N191K/S529G/P527V, N191K/S529G/P527Y, N191K/S529G/F525Y/P527Y, N191K/S529G/F525Y/P527Y/G6A, and N191K/S529G/S505P.

10. A protein comprising the amino acid sequence set forth in SEQ ID NO: 1 having glucose dehydrogenase activity, wherein the protein has an amino acid mutation selected from the group consisting of N191K/S529G/S505P/N46E, N191K/S529G/S505P/N240E, N191K/S529G/S505P/N274E, N191K/S529G/S505P/N275E, N191K/S529G/S505P/N370K, and N191K/S529G/S505P/N370E.

11. The protein according to claim 6, wherein in the protein comprising the amino acid sequence set forth in SEQ ID NO: 1, 16 residues are deleted from the N-terminal sequence thereof, and the Ser residue at position 17 is substituted by Met.

12. The protein according to claim 6, wherein in the protein comprising the amino acid sequence set forth in SEQ ID NO: 1, 23 residues are deleted from the N-terminal sequence thereof, and Met-Thr-Asp-Ser-Thr-Leu-Asn, Met-Thr-Asp-Ser-Thr-Leu-Asn, Met-Asn-Thr-Thr-Thr-, or Met-Ala-Pro-Glu- is added.

13. A method for analyzing glucose, comprising measuring a glucose concentration in a sample using a protein according to claim 1 or claim 6.

14. A glucose assay kit comprising a protein according to claim 1 or claim 6, and a mediator.

15. An enzyme electrode comprising a protein according to claim 1 or claim 6 immobilized on an electrode surface.

16. A glucose sensor comprising an enzyme electrode according to claim 15 as a working electrode.

* * * * *

SEQUENCE LISTING

<160> NUMBER OF SEQ ID NOS: 2

<210> SEQ ID NO 1
<211> LENGTH: 589
<212> TYPE: PRT
<213> ORGANISM: Sclerotinia sclerotiorum

<400> SEQUENCE: 1

```
Met Asn Arg Leu Leu Pro Ala Val Ala Leu Ala Ser Leu Ala Val Ala
 1               5                  10                  15

Ser Pro Glu Leu Asn Leu Ala Tyr Asp Tyr Val Ile Val Gly Gly Gly
            20                  25                  30

Thr Ser Gly Leu Val Ile Ala Asn Arg Leu Ser Glu Leu Asn Val Thr
        35                  40                  45

Val Ala Val Ile Glu Ala Gly Asp Leu Gly Tyr Glu Asn Val Asn Ile
    50                  55                  60

Thr Asn Pro Ala Gly Tyr Gly Leu Ala Phe Gly Thr Asn Ile Asp Trp
65                  70                  75                  80

Ala Tyr Gln Ser Val Asn Gln Lys Tyr Ala Gly Asn Ala Thr Gln Thr
                85                  90                  95

Leu Arg Ala Gly Lys Val Ile Gly Gly Thr Ser Thr Ile Asn Gly Met
            100                 105                 110

Ala Tyr Thr Arg Ala Glu Asp Val Gln Ile Asp Ala Trp Glu Ala Leu
        115                 120                 125

Gly Asn Asp Gly Trp Asn Trp Glu Asn Leu Phe Pro Tyr Tyr Lys Lys
    130                 135                 140

Ser Gln Arg Leu Glu Pro Pro Thr Ala Ala Gln Ala Glu Ser Gly Ala
145                 150                 155                 160

Thr Tyr Asp Pro Ser Ala Asn Gly Val Asp Gly Pro Leu Lys Val Gly
                165                 170                 175

Trp Leu Asn Asn Leu Ala Asn Asp Asp Phe His Ile Thr Leu Asn Asp
            180                 185                 190

Thr Tyr Ala Ser Leu Gly Val Phe Ala Asn Glu Asp Val Asn Thr Gly
        195                 200                 205

Arg Met Val Gly His Asn Arg Tyr Pro Ala Thr Tyr Asp Ser Thr Leu
    210                 215                 220

Asn Val Arg His Asp Ala Gly Arg Ala Tyr Tyr Tyr Pro Ile Ala Asn
225                 230                 235                 240

Arg Thr Asn Leu His Leu Tyr Pro Asn Thr Met Ala Gln Arg Leu Thr
                245                 250                 255

Trp Lys Ser Gly Ala Asp Ile Pro Thr Thr Asn Gly Val Glu Val Leu
            260                 265                 270
```

```
Ala Asn Asn Ser Ser Ile Pro Tyr Thr Ile Ser Ala Asn Ser Glu Val
            275                 280                 285

Ile Leu Ser Ala Gly Ala Leu Ala Ser Pro Leu Leu Leu Glu Leu Ser
        290                 295                 300

Gly Ile Gly Asn Pro Ser Ile Leu Asn Lys Tyr Asn Ile Pro Val Val
305                 310                 315                 320

Val Asp Leu Pro Thr Val Gly Glu Asn Leu Gln Asp Gln Thr Asn Asn
                325                 330                 335

Gly Leu Ala Tyr Thr Val Ser Glu Asp Ala Ser Phe Ser Gly Val Gly
            340                 345                 350

Thr Leu Val Ala Tyr Pro Ser Ala Ala Gln Val Phe Gly Ser Glu Ile
                355                 360                 365

Gln Asn Ile Ser Thr His Val Leu Asp Ser Leu Pro Ser Tyr Ala Ala
            370                 375                 380

Gln Val Ser Ala Ala Ser Gly Asn Ile Thr Lys Ala Ala Asp Leu Leu
385                 390                 395                 400

Glu Phe Phe Lys Ile Gln Tyr Asp Leu Ile Phe Ser Ser Thr His Pro
                405                 410                 415

Ile Pro Met Ala Glu Ile Leu Val Met Pro Ser Thr Thr Gly Phe Thr
            420                 425                 430

Thr Glu Tyr Trp Ala Leu Leu Pro Phe Ala Arg Gly Asn Ile His Ile
                435                 440                 445

Thr Ser Ser Ile Pro Gly Thr Pro Ala Ala Ile Asn Pro Asn Tyr Tyr
            450                 455                 460

Met Leu Asp Trp Asp Ile Thr Ser Gln Phe Thr Thr Ala Lys Phe Ile
465                 470                 475                 480

Arg Ser Ile Tyr Ala Thr Ser Pro Leu Ser Asn Leu Val Gly Ser Glu
                485                 490                 495

Thr Lys Pro Gly Leu Glu Thr Val Ser Ala Asn Ala Thr Glu Ala Glu
            500                 505                 510

Trp Ser Glu Trp Ile Lys Ala Gly Tyr Arg Ser Asn Phe His Pro Val
                515                 520                 525

Ser Thr Ala Ala Met Met Pro Arg Glu Val Gly Val Val Asp Ser
            530                 535                 540

Arg Leu Lys Val Tyr Gly Thr Ser Asn Val Arg Val Val Asp Ala Ser
545                 550                 555                 560

Ile Leu Pro Met Gln Val Cys Gly His Leu Val Ser Thr Leu Tyr Ala
                565                 570                 575

Val Ala Glu Arg Ala Ala Asp Leu Ile Lys Glu Glu Ile
            580                 585

<210> SEQ ID NO 2
<211> LENGTH: 588
<212> TYPE: PRT
<213> ORGANISM: Aspergillus niger

<400> SEQUENCE: 2

Met Leu Phe Pro Ser Leu Ala Leu Ala Ala Phe Ser Leu Gly Val Thr
1               5                   10                  15

Ala Lys Ser His Ala Asp Ser Pro Ala His Tyr Asp Phe Val Ile Val
            20                  25                  30

Gly Gly Gly Thr Ser Gly Leu Val Val Ala Asn Arg Leu Ser Glu Leu
        35                  40                  45

Ser Asp Val Thr Val Ala Val Ile Glu Ala Gly Glu Ser Ala Leu Asn
```

```
            50                  55                  60
Asn Phe Asn Val Ser Asn Val Met Gly Tyr Ser Thr Ala Phe Gly Thr
 65                  70                  75                  80
Glu Val Asp Trp Ala Tyr Gln Thr Glu Asn Gln Thr Tyr Ala Gly Gly
                 85                  90                  95
Leu Gln Gln Thr Ile Arg Ala Gly Lys Ala Leu Gly Gly Thr Ser Thr
                100                 105                 110
Ile Asn Gly Met Ser Tyr Thr Arg Ala Glu Asp Val Gln Ile Asp Asn
                115                 120                 125
Trp Glu Val Leu Gly Asn Asp Gly Trp Asn Trp Lys Asn Leu Phe Gln
130                 135                 140
Tyr Tyr Lys Lys Ser Glu Gly Phe Gln Val Pro Thr Lys Asp Gln Ile
145                 150                 155                 160
Ala His Gly Ala Ser Tyr Asn Ala Ser Tyr His Gly Leu Asn Gly Pro
                165                 170                 175
Leu Lys Val Gly Trp Pro Asn Ser Met Thr Asn Ser Ser Val Phe Pro
                180                 185                 190
Val Leu Glu Gln Thr Phe Glu Lys Leu Gly Val Gln Tyr Asn Pro Asp
                195                 200                 205
Ser Glu Gly Gly Lys Met Val Gly Phe Thr Val His Pro Asp Thr Leu
                210                 215                 220
Asp Arg Glu Met Asn Val Arg Glu Asp Ala Ala Arg Ala Tyr Tyr Trp
225                 230                 235                 240
Pro Tyr Glu Ala Arg Ser Asn Leu Lys Ile Ile Ser Asn Thr Arg Ala
                245                 250                 255
Asn Lys Val Ile Trp Ala Asn Thr Thr Gln Gly Glu Ala Val Ala Val
                260                 265                 270
Gly Ile Glu Val Thr Asn Ala Tyr Gly Thr Glu Thr Ile Tyr Ala Asp
                275                 280                 285
Lys Glu Val Ile Leu Ser Ala Gly Ala Leu Arg Ser Pro Ala Ile Leu
                290                 295                 300
Glu Leu Ser Gly Ile Gly Asn Pro Asp Val Leu Asn Lys His Asn Ile
305                 310                 315                 320
Pro Val Lys Val Asn Ile Thr Thr Val Gly Glu Asn Leu Gln Asp Gln
                325                 330                 335
Thr Asn Asn Ala Leu Ser Trp Glu Gly Val Asp Thr Leu Thr Gly Leu
                340                 345                 350
Ala Thr Phe Ser Val Leu Pro Ser Val Asn Gln Leu Tyr Gly Asp Asn
                355                 360                 365
Val Thr Ala Leu Ala Ser Tyr Val Lys Ser Gln Leu Ala Ser Tyr Ala
                370                 375                 380
Lys Thr Val Ala Ser Ser Asn Gly Ala Val Lys Glu Ala Asn Leu
385                 390                 395                 400
Val Glu Ala Phe Glu Arg Gln Tyr Asp Leu Ile Phe Asn Ser Gln Val
                405                 410                 415
Pro Tyr Thr Glu Val Val Phe Ala Pro Ser Gly Asn Ser Phe Ala Val
                420                 425                 430
Glu Tyr Trp Pro Leu Leu Pro Phe Ser Arg Gly Ser Val His Ile Gln
                435                 440                 445
Ser Ala Asn Ala Ser Asp Tyr Pro Ala Ile Asn Pro Asn Tyr Phe Met
                450                 455                 460
Phe Asp Gln Asp Ala Glu Ala Gln Val Thr Val Ala Gln Tyr Ile Arg
465                 470                 475                 480
```

```
Lys Ala Leu Gly Thr Ala Pro Leu Asn Ser Leu Val Gly Glu Glu Val
                485             490             495

Ser Pro Gly Leu Asp Val Leu Pro Ala Ser Ala Ser Ser Ala Thr Trp
            500             505             510

Thr Lys Trp Val Lys Glu Asn Tyr Arg Thr Asn Tyr His Pro Val Gly
        515             520             525

Thr Thr Ser Met Leu Pro Arg Glu Lys Gly Gly Val Val Ser Pro Glu
    530             535             540

Leu Lys Val Tyr Gly Thr Lys Asn Val Arg Val Val Asp Ala Ser Val
545             550             555             560

Leu Pro Phe Gln Leu Cys Gly His Leu Thr Ser Thr Leu Tyr Ala Val
            565             570             575

Ala Glu Arg Ala Ser Asp Leu Ile Lys Glu Ser Tyr
            580             585
```